United States Patent [19]

Takahashi

[11] Patent Number: 4,847,075

[45] Date of Patent: Jul. 11, 1989

[54] HYDRATED ALUMINUM SILICATE ADSORBENT SUPPORTING REDUCTIVE SUBSTANCE

[75] Inventor: Hidehiko Takahashi, Tokyo, Japan

[73] Assignee: Yakurigaku Chuo Kenkyusho, Tokyo, Japan

[21] Appl. No.: 387,554

[22] Filed: Jun. 11, 1982

[30] Foreign Application Priority Data

Jun. 12, 1981 [JP] Japan .................................. 56-90651

[51] Int. Cl.$^4$ ........................ A61K 7/135; A61K 9/07; A61K 9/14; C01G 3/00
[52] U.S. Cl. ........................................ 424/62; 423/44; 423/118; 514/859; 514/947; 514/949; 514/969
[58] Field of Search ........................... 424/62; 454/357

[56] References Cited

U.S. PATENT DOCUMENTS

| | | | |
|---|---|---|---|
| 1,629,096 | 5/1927 | Davis | 424/62 |
| 2,914,374 | 11/1959 | Harris et al. | 424/62 X |
| 3,800,809 | 4/1974 | Saad et al. | 424/62 X |
| 3,838,966 | 10/1974 | Barchas et al. | 424/62 |
| 3,892,845 | 7/1975 | Cunningham et al. | 424/62 |

FOREIGN PATENT DOCUMENTS

| | | | |
|---|---|---|---|
| 753037 | 1/1971 | Belgium | 424/62 |
| 1251467 | 10/1967 | Fed. Rep. of Germany | 424/68 |
| 2451918 | 5/1976 | Fed. Rep. of Germany | 424/357 |
| 45-15391 | 5/1970 | Japan | 424/62 |
| 0015429 | 2/1980 | Japan | 424/62 |
| 136118 | 7/1980 | Japan | 514/948 |

OTHER PUBLICATIONS

Merck Index, Ninth Edition, 1976, p. 4136.

*Primary Examiner*—Dale R. Ore
*Attorney, Agent, or Firm*—Armstrong, Nikaido, Marmelstein, Kubovcik & Murray

[57] ABSTRACT

An absorbent prepared by supporting an organic or inorganic reductive substance on hydrated aluminum silicate is useful as a pharmaceutical or as an absorbent for precious metal complexes such as gold complex, silver complex and the like.

6 Claims, No Drawings

HYDRATED ALUMINUM SILICATE ADSORBENT SUPPORTING REDUCTIVE SUBSTANCE

This invention relates to a hydrated aluminum silicate adsorbent supporting a reductive substance, and more particularly to a hydrated aluminum silicate adsorbent supporting a reductive substance which is useful as a pharmaceutical or as an adsorbent for precisous metal complexes such as gold complex, silver complex or the like.

Previously, the present inventor developed an adsorbent capable of adsorbing even anionic substances strongly by reforming the faults of the generally used aluminum silicate type adsorbent (Japanese Patent Kokai (Laid-Open) No. 136,118/80).

In order to further improve the adsorbing ability of this anion-adsorbing aluminum silicate adsorbent and further increasing its adsorbing capacity, it was attempted first of all to use various substances in combination with said aluminum silicate adsorbent. However, such an attempt could not attain a great success. Thus, as the next step, various additive substances were added in synthesizing hydrated aluminum silicate, and the substances thus obtained were examined for adsorbing performances. As the result, it was found that, if an organic or inorganic reductive substance is used as said additive substance, the resulting substance exhibits excellent performances as a pharmaceutical or as an adsorbent for precious metal complexes. This invention was accomplished based on the above-mentioned finding.

The hydrated aluminum silicate was synthesized by adding silica to a strongly acidic solution of an aluminum compound such as aluminum sulfate, and then gradually neutralizing the mixture with an alkali until it becomes weakly acidic and further neutral, as mentioned in Japanese Patent Kokai (Laid-Open) No. 136,118/80. By the investigation of its X ray diffraction pattern, this hydrated aluminum silicate has been revealed to be amorphous. According to differential thermal analysis, it shows an endothermic peak at 60° C. due to free water and adsorbed water, endothermic peaks at 215° C. and 320° C. due to the OH group of polymerized aluminum hydroxide ion and a small exothermic peak at ca. 1,000° C.

According to this invention, an inorganic or organic reductive substance is added in synthesizing this hydrated aluminum silicate, by which a hydrated aluminum silicate supporting a reductive substance is obtained. As the reductive substance to be supported, the followings can be referred to. Thus, as inorganic substances, thiosulfates, sulfites, sodium hydrogen sulfite (sodium bisulfite), iron salts, copper salts, sulfides, tripolyphosphates, and the like can be referred to. As organic substances, Rongalit, hydroquinone, formaldehyde, paraformaldehyde, thiourea, cysteine, thioglycerin, thiosorbitol, Vitamin E, reduced form of ubiquinone, glutathione, succinic acid and the like can be referred to. These reductive substances may be supported either alone or in combination of two or more.

EXAMPLE 1

Production of Hydrated Aluminum Silicate Supporting Reductive Substance

A solution prepared by diluting 2.5 g of 20% $SiO_2$ sol with 100 ml of water was added to a solution prepared by dissolving 18.0 g of $Al_2(SO_4)_3.16 \sim 18H_2O$ in 100 ml of water. Then, the mixture was adjusted to pH 2.0 with 10% $H_2SO_4$. While dropping N/10 NaOH, its pH was gradually increased and finally adjusted to an end point of 5.0. During this procedure, one or more kind(s) of reductive substance is added in an amount of 0.5 g to 10 g.

After ageing the reaction mixture for an appropriate period of time, it was filtered by centrifugation and the precipitate was collected. The precipitate was washed with 150 ml of pure water and then precipitated by centrifugation, and this procedure was repeated several times. Thereafter, the precipitate was brought into dryness under reduced pressure and pulverized.

For example, in case that 0.5 g of sodium thiosulfate and 32 mg of $Na_2SO_3$ were added as the reductive substance, the yield of the intended product was about 7 g (this product is sometimes referred to as "Lot No. 96").

EXAMPLE 2

Production of Hydrated Aluminum Silicate Supporting Reductive Substance

A solution prepared by diluting 2.5 g of 20% $SiO_2$ sol with 150 ml of water was added to a solution prepared by dissolving 28.6 g of $Al_2(SO_4)_3.16 \sim 18H_2O$ into 150 ml of water, and pH of the mixture was adjusted to 2.0 with 10% $H_2SO_4$.

pH of the mixture was brought to 5.0 while dropping 10% solution of hexamethylenetetramine with stirring. During this procedure, one or more kind(s) of reductive substance was added in an amount of 2.0 g to 40 g.

After ageing the reaction mixture for an appropriate period of time, it was filtered by centrifugation to collect the precipitate. The precipitate was washed with 300 ml of pure water and then precipitated by centrifugation, and this procedure was repeated several times. Thereafter, the precipitate was brought to dryness under reduced pressure and then pulverized until its size reached an appropriate mesh.

For example, in case that 2.0 g of sodium thiosulfate and 126 mg of $Na_2SO_3$ were added as reductive substance, yield of the intended product was 10.5 g (this product is sometimes referred to as "Lot No. 113").

EXAMPLE 3

Melanin-adsorbability Increasing Effect Brought About by Supporting Reductive Substance on Hydrated Aluminum Silicate Air was introduced for 3 days at a rate of 5 ml/minute into a solution prepared by dissolving 1.0 g of L-Dopa into a mixture of 50 ml of distilled water and 350 ml of M/10 phosphate buffer solution (pH 8.0) to synthesize Dopa melanin. The yield was about 650 mg.

An NaOH solution (pH 11.2) containing 0.02% of this Dopa melanin was mixed with a phosphate buffer solution (pH 5.5) at a ratio of 1:1 to prepare a 0.01% Dopa melanin test solution (pH 6.2).

Adsorbing abilities of adsorbents were compared by adding various adsorbents to this test solution at appropriate concentration, contacting the adsorbents with the solution for one hour with stirring, and measuring the removal rate of melanin.

Melanin concentration of the solution was determined by measuring its light absorbance at a wave length of 470 m$\mu$ (or nM) by means of a photoelectric colorimeter and comparing it with a beforehand prepared calibration curve.

In the following table are shown the adsorbing abilities of an adsorbent of this invention prepared by supporting, on hydrated aluminum silicate, sodium thiosulfate as a reductive substance (Lot No. 96), an adsorbent prepared by supporting no reductive substance on hydrated aluminum silicate, i.e. hydrated aluminum silicate itself (this is sometimes referred to as "Lot No. 61") and an adsorbent prepared by merely adding sodium thiosulfate to Lot No. 61 externally, together with adsorbing abilities of an adsorbent consisting of pharmacopoeial kaolinite only and an adsorbent consisting of a mixture of pharmacopoeial kaolinite and sodium thiosulfate. It is apparent from the table that the adsorbent of this invention has an increased adsorbing ability owing to the supported reductive substance.

|  | Reductive substance supported | Concentration at the time of use (%) | Removal rate of melanin (%) |
|---|---|---|---|
| Lot No. 61 | (—) | 1.0 | 48.3 |
| Lot No. 61 + Sodium thiosulfate | (—) | 1.0<br>2.0 | 51.9 |
| Pharmacopoeial kaolinite | (—)<br>(—) | 1.0<br>2.0 | 9.5<br>12.3 |
| Pharmacopoeial kaolinite + Sodium thiosulfate | (—) | 1.0<br>1.0 | 12.3 |
| Pharmacopoeial kaolinite + Sodium thiosulfate | (—) | 2.0<br>1.0 | 18.8 |
| Lot No. 96 (Present Invention) | Sodium thiosulfate | 0.5<br>1.0 | 83.1<br>95.8 |

EXAMPLE 4

The Change in Melanin-Adsorbability Depending on the Reductive Substance Supported By the same procedure as in claim Example 3, the melanin-adsorbabilities of hydrated aluminum silicates supporting various reductive substances were tested to obtain the results shown in the following table.

| Lot No. | Reductive substance supported | Removal rate of melanin (Adsorbent concentration 1%; Contact time 1 hr.) |
|---|---|---|
| 61 | — | 48.9 |
| 78 | Cysteine | 73.0 |
| 96 | Hypo | 94.6 |
| 127 | Thioglycerin | 63.8 |
| 128 | Thiourea | 61.5 |
| 59 | Formaldehyde | 72.5 |

EXAMPLE 5

Action of Removing Free Fatty Acid

The ability of the adsorbent of this invention to remove free fatty acid was studied by adding the adsorbent of this invention to solution of free saturated fatty acid or unsaturated fatty acid such as lauric acid (12:0), palmitic acid (16:0), linoleic acid (18:2), linolenic acid (18:3) or the like so that the concentration of the adsorbent came to several percents. The change in the concentration of fatty acid was semiquantitatively followed by TLC (silica gel G; ether:benzene:ethanol:acetic acid=40:50:2:0.2).

The fatty acid removing ability of hydrated aluminum silicate markedly increased by the supported reductive substance.

EXAMPLE 6

Metal Complex Adsorbability

As an example of precious metal complex, silver thiosulfate complex was selected.

The solution of silver thiosulfate complex was prepared in the following manner, under consideration of the waste solution of fixation of photographic film. Thus, it was prepared by dissolving 200 g of sodium thiosulfate into 1 liter of water, adding 5 g of $AgNO_3$ to the solution and adjusting its pH to 7.0.

Various adsorbents were added to the abovementioned silver complex solution and contacted therewith for 3 hours, after which the silver-adsorbabilities were compared. The silver concentration of the solution was measured by means of Shimazu Atomic Absorption/Flame Spectrophotometer (AA-646).

As shown in the following table, the increase in adsorbability by the supporting of reductive substance was remarkable. The merit of hydrated aluminum silicate supporting reductive substance consists in that the adsorbed silver thiosulfate ion is immediately reduced to metallic silver and leaves the site of adsorption as a silver mass so that the adsorption of silver complex ion can recur almost unlimitedly. In the case of simple aluminum silicate, contrariwise, the adsorbability reaches a saturation sooner or later.

The following table shows comparison of silver complex adsorbabilities of reductive substance-supporting hydrated aluminum silicates synthesized according to the formulation shown in Example 2 and reductive substance-nonsupporting hydrated aluminum silicates.

| Lot No. | Reductive substance supported | Amount (g) | Removal rate of silver complex at 40° C. after 3 hrs. (%) Concentration of adsorbent (%) | | |
|---|---|---|---|---|---|
| | | | 1.0 | 2.0 | 5.0 |
| 112 | — | — | | | 41.9 |
| 114 | — | — | | | 43.8 |
| 113 | Hypo | 2.0 | | | 55.8 |
| 117 | | 2.0 | | | 61.5 |
| 119 | | 5.0 | 26.8 | 50.1 | |
| 118 | | 10.0 | | 62.8 | |
| 120 | | 10.0 | | 68.2 | |
| 121 | | 20.0 | 58.9 | | |

-continued

| Lot No. | Reductive substance supported | Amount (g) | Removal rate of silver complex at 40° C. after 3 hrs. (%) Concentration of adsorbent (%) | | |
|---|---|---|---|---|---|
| | | | 1.0 | 2.0 | 5.0 |
| 122 | Na$_2$S | 2.0 | 45.0 | | |
| 123 | | 5.0 | 74.5 | | |
| 124 | Na$_2$S + Hypo | 2.5 .2.5 | 74.3 | | |
| 126 | Na$_2$SO$_3$ | 5.0 | | 22.0 | |
| 130 | Rongalit | 10.0 | | | 58.8 |
| 140 | Hypo + Formaldehyde | 20.0 20.0 | 95.4 | | |

EXAMPLE 7

Therapeutic Effect of the Reductive Substance-Supporting Hydrated Aluminum Silicate as an Agent for Treating Cutaneous Diseases As an example of the hydrated aluminum silicate supporting reductive substance, the adsorbent Lot No. 96 obtained in Example 1 was used after pulverizing it to a granular size of 11μ or less, and its therapeutic effect on various cutaneous diseases was investigated.

The ointment used had the following composition. Hereinafter, this ointment will be referred to as "Ointment 96".

| Base | Content of Lot No. 96 |
|---|---|
| A mixture prepared by formulating Carbowax 400 and Carbowax 4000 at a ratio of 1:2 | 5% |

(a) Pigment anomaly

When "Ointment 96" was applied to the diseased part 2-3 times a day, the chloasma having a size of small beans showed a disappearance of pigment in 2-3 weeks, and almost completely disappeared within 3 months.

In a test using five 30-45 aged women and five 50-65 aged men, the results obtained by applying the ointment for 3 months were as follows.

Effect of application for 3 months on chlosma

| Ineffective | | Effective | | Markedly effective | |
|---|---|---|---|---|---|
| ♂ | ♀ | ♂ | ♀ | ♂ | ♀ |
| 0/5 | 0/5 | 1/5 | 2/5 | 4/5 | 3/5 |

Ineffective: Disappearance of pigment was not observed.
Effective: A marked disappearance of pigment was observed.
Markedly effective: Pigment became almost unnoticeable.
(The effect was judged by photography using Nicon Medical Nicol.)

On pigmented nevus, the ointment had an effect so far as the disappearance of melanin pigment was concerned.

Effect of application for 3 months on pigmented nevus

| Ineffective | | Somewhat effective | | Effective | | Markedly effective | |
|---|---|---|---|---|---|---|---|
| ♂ | ♀ | ♂ | ♀ | ♂ | ♀ | ♂ | ♀ |
| 0/5 | 0/5 | 1/5 | 0/5 | 3/5 | 2/5 | 1/5 | 3/5 |

Ineffective: Disappearance of pigment was not observed.
Somewhat effective: Disappearance of pigment was observed.
Effective: A marked disappearance of pigment was observed.
Markedly effective: A decrease in the size of nevus itself was also observed.
(The effect was evaluated in the same manner as above.)

(b) Acne vulgaris

Using 10 male patients and 10 female patients, "Ointment 96" was applied to the diseased part several times a day, and the effect was evaluated after 3 months.

| Ineffective | | Effective | | Markedly effective | |
|---|---|---|---|---|---|
| ♂ | ♀ | ♂ | ♀ | ♂ | ♀ |
| 0/10 | 0/10 | 2/10 | 3/10 | 8/10 | 7/10 |

Ineffective: No effect was observed.
Effective: An obvious effect was observed.
Markedly effective: The disease was nearly cured.
(The effect was evaluated in the same manner as above.)

What is claimed is:

1. An adsorbent comprising at least one reductive substance supported on hydrated aluminum silicate.

2. An adsorbent according to claim 1, wherein said at least one reductive substance is a melanin pigment-decomposing substance.

3. An adsorbent according to claim 2, wherein said melanin pigment-decomposing substance is at least one compound selected from the group consisting of thiosulfate, thioglycerin, thiourea and formaldehyde.

4. An adsorbent according to claim 1, wherein said hydrated aluminum silicate is produced by reacting an aluminum compound with a silicon compound in an acidic medium; dropwise adding an alkaline substance to said medium, so as to provide a weakly acidic or neutral medium; and aging the resulting medium.

5. An adsorbent comprising at least one reductive substance supported on hydrated aluminum silicate wherein the adsorbent is prepared by adding said at least one reductive substance when synthesizing said hydrated aluminum silicate.

6. An absorbent according to claim 5, wherein said adsorbent is produced by reacting an aluminum compound with a silicon compound in an acidic medium; dropwise adding an alkaline substance to said medium, so as to provide a weakly acidic or neutral medium, while adding said at least one reductive substance; and aging the resultng medium.

* * * * *